US00PP21283P3

(12) United States Plant Patent
Benardella

(10) Patent No.: US PP21,283 P3
(45) Date of Patent: Sep. 14, 2010

(54) MINI-FLORA ROSE PLANT NAMED 'BENSWISE'

(50) Latin Name: *Rosa hybrida*
Varietal Denomination: BENswise

(75) Inventor: Frank Benardella, Millstone Township, NJ (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 12/322,228

(22) Filed: Jan. 30, 2009

(65) Prior Publication Data

US 2010/0199394 P1 Aug. 5, 2010

(51) Int. Cl.
*A01H 5/00* (2006.01)

(52) U.S. Cl. ..... Plt./121

(58) Field of Classification Search ..... Plt./121, Plt./148, 149
See application file for complete search history.

*Primary Examiner*—Kent L Bell

(57) ABSTRACT

The fragrant, magenta-rose colored flowers of his new invention are held nicely above the foliage, primarily in small clusters. The plant is of a medium size and upright growing habit and rarely seen without some color.

1 Drawing Sheet

CROSS REFERENCE

This invention bears resemblance to 'BENiowa' (not patented), a rose from this same breeding program, sharing the same seed parent of 'KORivo' (not patented). Both plants are upright and well branched, growing to about the same average height of three feet, even though 'BENiowa' was registered as a floribunda. Both have fragrant, hybrid tea form flowers with similar petal counts, borne in small clusters. The new invention has flowers of a magenta-rose, while 'BENiowa' has flowers of white with a band of red along the margins and blending down into the petals.

This new invention may also be compared to 'BENfig' (U.S. Plant Pat. No. 8,020) from the same breeding program, which shares the same pollen parent of 'KORmulen' (not patented). Both have relatively compact, upright, and well-branched plant habits. Both bloom near continuously with hydrid tea from flowers. They have similar petal counts with moderately thick petals and a satiny to velvety texture. 'BENfig', being a miniature rose, is an overall smaller plant than this new invention. The flowers of 'BENfig' are white edged with pink compared to flowers of magenta-rose on this new invention.

Genus and species: *Rosa hybrida.*

Varietal denomination: 'BENswise'.

BACKGROUND OF THE INVENTION

The present invention relates to a new and distinct variety of hardy, bush-type rose plant. This new variety is from a single seedling originated by Frank A. Benardella under controlled conditions in a greenhouse in Millstone Township (formerly Englishtown), N.J., by crossing the following two rose plants:

- The seed parent is 'KORivo' (not patented), a floribunda rose with cream-ivory flowers.
- The pollen parent is 'KORmulen' (not patented; trade name, Laguna), a red hybrid tea rose.

The new invention is easily distinguished from its parents:

| | THIS PRESENT INVENTION, 'BENswise' | SEED PARENT, 'KORivo' | POLLEN PARENT, 'KORmulen' |
|---|---|---|---|
| CLASS | Mini-Flora | Floribunda | Hybrid tea |
| BLOOM COLOR | Magenta-rose | Cream-Ivory | Medium-red |
| BLOOM HABIT | Borne singly and in small clusters; larger clusters on candelabra stems, when present; near continuous throughout the season. | Borne in large sprays and clusters; near continuous throughout the season. | Borne primarily singly; repeats in cycles throughout the season. |
| FLOWER FRAGRANCE | Double Moderate Fragrance | Semi-double Moderate to strong Fragrance | Fully double Strong Fragrance |
| PLANT HABIT | Upright, 18 to 36 inches with width becoming about ⅔ its height. | 4 to 5 feet tall and well rounded | Upright, 3 to 4 feet. |

The primary goal of this breeding program is to produce unique roses with award winning, hybrid tea form on plants having favorable attributes that will increase public appeal. To achieve this goal roses are selected for this hybridizing program primarily by the quality of their hybrid tea form. Pertaining to this particular cross, the seed parent, 'KORivo', has hybrid tea form flowers with very high centers as they begin to open. The pollen parent for this new invention, 'KORmulen', has been noted to pass on the trait of hybrid tea flower form in a wide range of colors. The resulting new cultivar has been named 'BENswise', with the trade name of Dejá Blu. Asexual reproduction of this new cultivar by cuttings, in Millstone Township, N.J., and Arroyo Grande, Calif., have shown that all distinguishing characteristics of this rose continually come true to form.

SUMMARY OF THE INVENTION

This present invention relates to a new and distinct variety of a hardy, bush type, rose plant, which has several features that distinguish it from other presently available roses. Its magenta-rose, hybrid tea form flowers are borne above the plant in such a manner that they stand out magnificently against the dark-green glossy foliage. Other characteristics that help distinguish it from all other varieties of which I am aware are:

- Its lack of thorns.
- Its flowers of a magenta-rose with little fade.
- It's near continuous bloom cycle.
- Flowers that open slowly.
- Its upright and compact habit.
- Its sweet fragrance.
- Its marcescent petals.
- A plant that grows and blooms very well, in both a greenhouse and outdoors, as a perennial garden decoration or in large containers.

BRIEF DESCRIPTION OF THE DRAWING

The accompanying illustration was taken in September, and is of 3-year-old plants of this new invention, growing in the ground in Arroyo Grande, Calif. The image, as presented, shows the plants at approximately one-third their actual size. Flowers and foliage of this new invention are visible in various stages of development. Color is as nearly correct as possible to make in a color illustration of the character.

BOTANICAL DESCRIPTION OF THE PLANT

Unless otherwise noted, the following observations, measurements, values and comparisons are from a five-year-old plant of *Rosa hybrida*, 'BENswise', as grown outdoors in Ipswich, Mass. The plant was received in Massachusetts in a 12-inch plastic nursery container in artificial soil mix in April, 2008. in July, 2008, it was transplanted into a 15-inch plastic container in a peat moss and compost mix. Observation was continued through October. Phenotypic expression may vary with environmental, cultural, and climatic conditions. Color references are made using The Royal Horticultural Society Colour Chart, except where common terms of color are used.

FLOWERS

Blooming habit was fast repeat to near continuous. Buds and flowers are borne in tight clusters, usually of three or four, and also singly. On the mature plant, new flowers grow up in such a manner they begin to open just after the old flowers become unsightly.

Buds were ovate with an acute tip and obtuse base. From plants out of the California greenhouse, buds were about ¾ inch long with a diameter of about 9/16 inch. In Massachusetts, buds would be about 11/16 inch long with a diameter of about ½ inch.

When fully expanded, blooms were not symmetrical, having diameters around 2 1/16 inches by 2 9/16 inches with a depth varying between 1 9/32 and 1 13/32 inches. (Coming out of the California greenhouse, fully expanded blooms were measured considerably larger: diameters varied from 3 2/16 inches by 3 5/16 inches to 3 11/16 inches by 3 15/16 inches; and depths varied from 1 5/16 to 1 6/16 inches, not respective to diameters. More of the blooms were near the larger size.) The blooms began to open with a flat upper profile and urceolate lower profile. The upper profile on the open flower was usually flattened convex. The lower profile became flattened convex.

Petalage was counted at 20 to 33 with 3 to 6 petaloids. Outer petal margins recurve gently as the petals unfurl. In the full open flower, at 50° to 70° F. petals lasted about 10 days on the plant before they started to wither. They did not drop readily from the receptacle. Fragrance was noted as mild to moderate and sweet.

Petals were of a medium thickness with excellent substance. The adaxial surface was slightly satiny to velvety. The abaxial surface was satiny. All veins were recessed on the adaxial surface. Main veins protruded a little on the abaxial surface as they radiated out from the point of attachment. Primary lateral veins protruded to a lesser degree. Outer petals were round to oblate, having an obtuse base and rounded, crenate, wavy margins that were notched on either side of the apex. Intermediate petals were broad fan shaped and margins were rounded and sometimes entire and sometimes emarginated. Inner petals were obtuse with rounded, entire margins. Apices were apiculate. The outer margins recurved slightly from the time they began to unfurl and increased a bit as the bloom opened. The outermost petals in the full-blown flower were measured 2 to 2 1/8 inches wide and 1 13/16 to 1 15/16 inches long.

Color when sepals first divide was a blend of a dark Cardinal Red, near 53A, and a dark Ruby Red, near 61A. During the first few days the adaxial surface of the petals was noted as a purple-red, near 61B, suffused with a blend of near 53A and near 61A. Basal area was a very pale yellow-green, between 154D and 1D, from the point of attachment, and became white, near 155D as it radiated out into the petal. The abaxial surface was between 61B and 61C, and lighter, near 59D, along the margins and veins, with areas first exposed when the sepals divided being near 61A. The basal area was near 1D from the point of attachment and became near 155D as it radiated outward. When half open, the adaxial surfaces of the outer petals lightened to between 64C and 66C. The reverse had become a Magenta Rose near 64D, suffused with near 61B. Inner petals were a Phlox Pink, near 62B, with a reverse of a Magenta Rose blend, near 64D suffused with near 64C. Basal areas of both surfaces were a light Primrose Yellow, near 4D from the point of attachment, and became near 155D radiating outward along the veins into the basal area.

When full blown, the adaxial surface of the outer petals had lightened only a little to between 64C to 64D and 66C, and with some suffusion near 60D and 64C. The basal area was a Sulphur Yellow, near 6D, from the point of attachment and radiating into the basal area. The abaxial surface had become near 64D, with near 57C, a Rose Bengal, toward the center of the petal and between 57B and 64D along the petal edges. Veins radiating from the basal area were near 155A. The basal area and point of attachment was near 1D. About five intermediate petals were lighter, with an adaxial surface of near 64D with a light suffusion and marginal area of near 60C. Their basal area was near 4C from the point of attachment, which became near 155D and radiated out into the basal area and along the veins. The reverse of these petals was a Spiraea Red, near 63B, with a Rhodamine Purple, near 68D, along the margins. Their basal area was near 4D from the point of attachment, which became near 155D, and radiated out into the basal area. The adaxial surface of the inner petals was near 62B and suffused very lightly with near 64C. On rare occasions, there was a steak of near 64C on the petal surface. The reverse was near 62C and suffused with near 64C, being darkest toward the basal area. The basal area of both surfaces was the same as found on the intermediate petals. Blooms age to a Magenta Rose near 186D, with outer petals remaining a little darker, between 186C and 66D, suffused with near 64C. The reverse of all petals had become Magnolia Purple, near 70D, suffused with near 63B.

Petaloids usually have white streaks visible on both surfaces, and may have a suffusion of near 63B and some streaking between 64C and 68A, but otherwise are the same color as the inner petals. They are misshapen, often with very ruffled margins. They may be a half petal with one edge being along the main vein; they may be oval shaped. The base narrows rapidly to the point of attachment, sometimes appearing as a filament and sometimes being attached with a filament. The smallest petaloid noted was 3/16 inch wide and 5/16 inch long, which did not include the filament to which it was attached. The largest petaloid was 1¾ inches wide and 2 9/16 inches wide, was narrow cordate with an oblique base.

Sepals: The flower has five, ovate-oblong sepals with attenuate apices and truncated bases, permanently attached to the receptacle. Before the sepals divided, they extended beyond the tip of the bud by ½ inch on the flowers observed. The outer surfaces of the sepals were semi-glossy. The color was a light yellow-green, between 145A and 145B, in the basal area and up through the center, and darker, near 144A, toward and along the margins and apices. The basal area and up through the center of the inside surfaces was a very light yellow-green, near 145C. Along the margins was a darker yellow-green: on the two outer sepals it was near 147B; on the three innermost sepals it was near 146C. Apices and foliar appendages were a darker green, near 141A. The outer surface of the two outermost sepals was slightly coarse with a few stipitate glands near the base and a smattering of hairs across the surface. Foliar appendages and apices were glabrous. There were three or more lanceolate, foliar appendages along each margin, with stipitate glands up to the first foliar appendage. On the foliar appendages, there were stipitate glands also along those margins toward the apex and one at the tip. The two innermost sepals were covered with a thicker and appressed pubescence, had ciliated margins, and the only gland was at the tip of the apex. The one sepal in-between the inner and outer sepals displayed characteristics of both the inner and outer sepals, dividing down the center. It had foliar appendages along only one margin, a single gland at the apex, and a few stipitate glands near the base on the side with the foliar appendage. Inside surfaces of all sepals had a fine, wooly covering that became heavier and somewhat matted toward the apex. The sepals rolled back well ahead of the petals.

Receptacles on the newly opened flowers had a diameter of 9/32 to 10/32 inch with a height most often of 6/16 inch. On flowers half open at exhibition stage, diameters had increased to 11/32 and heights were found at 9/32 to 13/32 inch. The color of the receptacle was a medium yellow green, between 144B and 144A. The surface was semi-glossy and smooth with a smattering of appressed hairs. The top of the receptacle was oval with a diameter 12/32 by 11/32 inch. The color was a very light yellow-green, near 154D. There was a thick stand of white hairs, near 159C, between the filaments and styles.

Peduncles are straight and very strong. Their girth was most often ⅛ inch but varied from 7/64 to 10/64 inch. Lengths varied from 2⅛ to 2½ inch. The surface appeared glabrous but had a sparse covering of appressed hairs. The color was a medium yellow-green varying between 146C and 146A.

REPRODUCTIVE ORGANS

Stamens, filaments and anthers are arranged regularly around the styles, attached to the outer rim of the receptacle in two rows, staggered. On the full open flower, the filaments in the inner row were about 5/32 inch long and those in the outer row were about 7/32 inch long. Approximately the lower three-fourths was a Spiraea Red near 63B, and the upper one-fourth was Empire Yellow, near 11D. The abaxial surface of only the outer row of filaments appeared different: much lighter toward the base, near 62D, became near 11D at the top, and the colors blended together in-between. Total quantities varied from 61 to 76. Anthers were an Orange Buff, near 20C, with pollen sacs and pollen near 22A, Yellow Ochre.

Pistils, styles and stigmas were about half the quantity as stamens. Styles were thin, straight, and very uneven in length, varying from 3/32 to 11/32, and lengths in any one flower varied by 6/32 to 8/32 inches. Their color was near 163B right below the stigma, becoming near 159C at their bases. Stigmas were between 11C and 158A.

Hips were rounded-urceolate, being orbicular with only the top edge flaring out slightly. Diameters were measured from 14/32 to 19/32 inches with a height of ½ to ¾ inch. Colors on record for these hips is bright orange, near 169D and near 171B. Seeds protrude from the top on the mature hip.

PLANT

The plant of this new rose is upright growing, with good vigor and moderately full branching, to a mature height of 18 to 36 inches. Widths observed varied from 14 to 30 inches, usually relative to its height. Growth originated from a single cane, having a diameter of 13/16 inch. The first canes originating near the base of the main cane usually had a diameter of about ½ inch. Primary and secondary laterals from these canes had diameters of 12/32 to 15/32 inch at their bases. Flowering stems generally had a diameter about 5/32 inch and lengths varied from 3¼ to 5⅞ inches. There were usually 4 to 7 nodes on flowering stems, with the longer stems usually having 6 or 7 nodes. New and old wood were glabrous. The color of the new wood was a light yellow-green, between 144C and 144B, and flushed with near 185B. As the canes aged, they lost the anthocyanin coloring and became a darker yellow-green, near 146A. The oldest wood had lightened and was a muted medium green, near 191B. Lenticels probably started to form in the third year of growth, forming parallel lines from the base of the oldest canes. Lenticels were near 191B and brown, near 200D.

Variations regarding the plant: A difference in day and night temperatures greater than around 30° F. can cause the plant to send up long, very fast growing canes. These originate at or near the base of the plant and are often referred to as candelabras because of the large number of blooms originating near the top of a usually long cane. On this new invention, these canes have been observed to extend about ten inches above the top of the crown of the plant and always terminate in a large cluster of flowers. As may be seen throughout the accompanying image and more fully along the upper right side of the image, the color of these canes was usually the same as new growth, being flushed the entire length with near 185B. They gradually become the same color as the older wood on the plant. The largest leaves are usually found on these candelabras.

FOLIAGE

Leaves generally had five to seven leaflets, though some only had three. Mature leaves were measured from 3¼ to 4 13/16 inches, regardless of the number of leaflets. On candelabra-type canes, some seven-leaflet leaves were measured up to 6½ inches long. Leaflets were broadly ovate and tapered gradually to a point at the apex. Serration was medium, mostly simple, and near even. There was a gland at the tip of each serrate. Leaflet bases were rounded except on terminal leaflets where they were oblate. Terminal leaflets were measured from 1¾ to 2½ inches long and 1¼ to 1½ inches wide, and up to 2⅞ inches long and 2 inches wide on leaves from the candelabras. Adaxial surfaces were glossy. Main veins were entirely recessed, primary lateral veins were mostly recessed, and secondary lateral veins were barely recessed. The abaxial surface was matte with main veins protruding entirely, primary lateral veins protruding somewhat and secondary lateral veins just barely. New leaflets had a medium-green adaxial surface between 143A and 144A, flushed with near 187A. The abaxial surfaces were more yellow-green, near 146D, and heavily flushed with between 185A and 187B. Main veins of abaxial surface of the young leaflets were near 183B; lateral veins were often flushed heavier than the leaflet surface. Anthocyanin coloration was absent from older foliage; the upper surface was between 147A and 139A, with the reverse near 147B.

Petioles varied from ½ to ⅞ inch, and up to 1 inch on leaves from the candelabras. Generally, petioles were shorter on the seven-leaflet leaves. The base was slanted making the petiole longer on one side than the other so occasionally one side was 2/32 to 3/32 longer than the other. The average girth was ⅛ inch. On the young leaf, the ridge along the crest of the adaxial surface was heavily flushed near 184B. The groove was lightly flushed with the same color. The underside was flushed with near 182A. On older foliage, there was a fine line along the ridge that appeared the same color as the leaflet surface, between 147A and 139A. The groove was much lighter, near 145C. The reverse was near 146B and became near 145B just before attaching to the stem. There were some stipitate glands along the ridge, and varying amounts of hair from none to many. In the grooves, there were none to many hairs with the heaviest concentration toward the juncture with the rachis and the first set of petiolules, where there were also occasional stipes and stipitate glands. There were also a few stipes in the groove between the stipules.

The rachis on the five-leaflet leaf varied from 26/32 to 31/32 inch long. The rachis on the seven-leaflet leaf was noted to be generally longer, between 1⅛ to 1½ inches long. The girth was found to be from just less than 1/16 inch on the five-leaflet leaves and 1/16 to 3/32 inch on the seven-leaflet leaves. The colors of the adaxial surface on young leaves were a bit lighter than on the petioles. The abaxial surface was the same as on the petiole. There were a few stipitate glands along the ridges. Hairs, stipes and a few stipitate glands were found in the grooves near and at the juncture with the petiolules.

Petiolules on the young foliage were darker along the ridges, between 176D and 185C, with the grooves flushed lighter with the same color. The abaxial surfaces were flushed with near 187C. Stipitate glands and a rare hair were observed on the ridges. Grooves were mostly glabrous, with hairs and stipes found near and at the base of each, with the exception of the petiolule to the terminal leaflet where the only hairs or stipitate glands were found right at the juncture with the leaflet blade. The reverse of all was glabrous. Lengths to terminal leaflets varied from 9/16 to 14/16 inch. Lengths to the basal leaflets varied from 3/32 to 3/16 inch. Occasionally these lengths varied from 1/32 to 3/32 in a pair of leaflets.

Stipules paired at the base of the petioles had 16/32 to 23/32 inch attached to the petiole, with pairs being even in length or lengths differing by up to ¼ inch. The tips were acuminate, usually the inside margin angled from the peduncle by up to 30°, and the outer margin ran parallel to the peduncle. Tips varied in length from 7/32 to 12/32 inch and lengths varied within a pair by 1/32 or 2/32 inch. Margins appeared dentate: often the margin of one was lined with stipitate glands and occasional gland-tipped serrates, while the margin of the other was lined with gland-tipped serrates with additional stipitate glands on the sides of and/or between some serrates. The color on the older foliage was a dark green, between 137B and 146A, on the upper surface. The reverse was near 146B with a small area of a much lighter green, near 145B, just before they attached to the petiole.

Variations regarding the leaves: Occasionally, attached to ridges of the petiole and or petiolules was a small simple leaf-like appendage, with no visible petiole. These were attached at random places along the ridges, though they were most often observed near the juncture of a pair of leaflets. Usually they were linear-subulate, or narrow oblong tapering at both ends, with acute or acicular apices. A central vein was visible the entire length of this leaflet, with a few lateral veins. Lengths noted varied from 5/32 to 9/32 inch and widths from 2/32 to 3/32 inch. Their coloring was the same as the leaflets.

Prickles are very rare on the canes of this new invention. A single prickle was found on a candelabra stem. It was 9/32 inch long, gradually narrowing to a point, and angled downward. The color was near 175A at the tip and became near 183C at the base. More commonly, prickles were observed on the abaxial surface of the rachis. They varied in length from 2/32 to 3/32 inch when present. The color was generally a Greyed-Orange-Purple, between 175A and 183B when young and gradually became a Greyed-Red, near 181B, on older foliage.

Resistance to blackspot, downy mildew, rust and insects was above average. The new invention is susceptible to powdery mildew.

The invention claimed is:

1. A new and distinct variety of rose plant is claimed, substantially as described and illustrated herein.

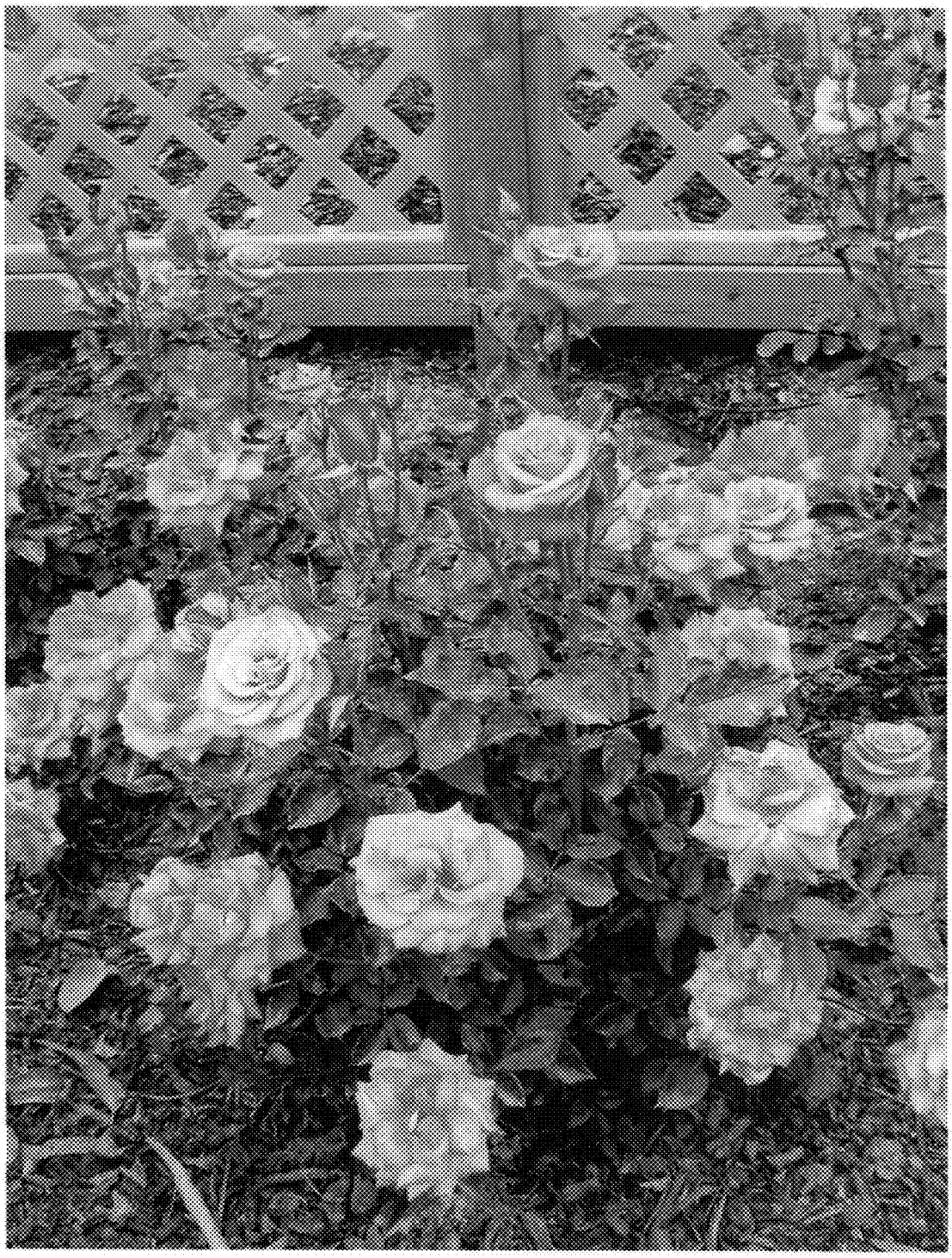

* * * * *